United States Patent
Brasher et al.

(10) Patent No.: US 9,832,990 B2
(45) Date of Patent: Dec. 5, 2017

(54) COMPOSITION COMPRISING AN ACTIVE SUBSTANCE AND A POLYALKYLENEOXIDE VINYLESTER GRAFT POLYMER

(75) Inventors: Laura L. Brasher, Clinton, NJ (US); Michael D. Capracotta, Canton, MI (US); Sonia Patterson, Detroit, MI (US); Murat Mertoglu, Ludwigshafen (DE); Marc Nolte, Mannheim (DE); Stefan Bechtel, Schwegenheim (DE); Kristin Klappach, Neustadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/041,902

(22) Filed: Mar. 7, 2011

(65) Prior Publication Data

US 2011/0218108 A1 Sep. 8, 2011

Related U.S. Application Data

(60) Provisional application No. 61/311,636, filed on Mar. 8, 2010, provisional application No. 61/318,804, filed on Mar. 30, 2010.

(51) Int. Cl.
*A01N 25/30* (2006.01)
*A01N 25/10* (2006.01)

(52) U.S. Cl.
CPC ............ *A01N 25/10* (2013.01); *A01N 25/30* (2013.01)

(58) Field of Classification Search
None
See application file for complete search history.

(56) References Cited

U.S. PATENT DOCUMENTS

| | | | |
|---|---|---|---|
| 4,849,307 A * | 7/1989 | Hoffmann et al. | 430/271.1 |
| 5,707,638 A * | 1/1998 | Losel et al. | 424/407 |
| 6,271,307 B1 | 8/2001 | Huff et al. | |
| 2004/0248741 A1* | 12/2004 | Gotsche et al. | 504/361 |
| 2007/0053944 A1 | 3/2007 | Vermeer | |
| 2008/0090886 A1 | 4/2008 | Gottsche et al. | |
| 2008/0255326 A1 | 10/2008 | Widmaier et al. | |
| 2008/0293828 A1 | 11/2008 | Bouillo et al. | |
| 2010/0047203 A1 | 2/2010 | Dieckmann et al. | |
| 2011/0245082 A1 | 10/2011 | Mertoglu et al. | |

FOREIGN PATENT DOCUMENTS

| | | | |
|---|---|---|---|
| EP | 0064379 | * 11/1982 | A01N 25/00 |
| EP | 0 953 347 | 11/1999 | |
| JP | 2004508306 | 3/2004 | |
| WO | WO 02/19821 | 3/2002 | |
| WO | WO 2005/036963 | 4/2005 | |
| WO | WO 2007/051742 | 5/2007 | |
| WO | WO 2007/051743 | 5/2007 | |
| WO | WO 2008/058848 | 5/2008 | |
| WO | WO 2009/073164 | 6/2009 | |
| WO | WO 2009/103760 | 8/2009 | |

OTHER PUBLICATIONS

Office Action dated Jan. 22, 2013, in U.S. Appl. No. 13/074,439.
Office Action dated May 23, 2012, in U.S. Appl. No. 13/074,439.
Liang, W., et al., "Stability of Dispersions in the presence of graft copolymer (II) adsorption of graft copolymers on titanium dioxide and the stability and rheology of the resulting dispersions", Langmuir, 2000, p. 1306-1310, vol. 16.
Haas, Stefan, et al., "Influence of polymeric surfactants on pesticidal suspension concentrates: dispersing ability, milling efficiency and stabilization power", Colloids and Surfaces A. Physiochem Eng. Aspects, 2001, p. 785-793, vol. 183-185.

(Continued)

*Primary Examiner* — Johann R Richter
*Assistant Examiner* — Danielle Sullivan
(74) *Attorney, Agent, or Firm* — Brinks Gilson & Lione

(57) ABSTRACT

A composition and a method of preparing the composition are provided herein. The composition comprises an active substance and a polymeric additive comprising at least one unit represented by the formula (I):

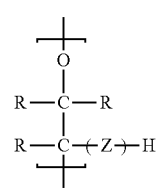

(I)

wherein each R is independently selected from the group of a hydrogen atom, an alkyl group, an aryl group, and combinations thereof; and Z comprises at least 10 units represented by the formula (II):

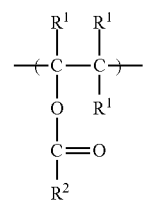

(II)

wherein each $R^1$ is independently selected from the group of a hydrogen atom, an alkyl group, an aryl group, a carbonyl group, a hydroxyl group, an ether group, and combinations thereof and $R^2$ is a $C_1$-$C_{10}$ hydrocarbon group. The polymeric additive further comprising at least one unit represented by the formula (III):

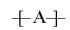

(III)

wherein A is an alkyleneoxy group having from 2 to 10 carbon atoms.

20 Claims, No Drawings

(56) References Cited

OTHER PUBLICATIONS

International Search Report dated Jul. 22, 2011, prepared in International Application No. PCT/EP2011/053261.
International Preliminary Report on Patentability dated Oct. 7, 2011, prepared in International Application No. PCT/EP2011/053261.
Office Action dated Mar. 10, 2015 in U.S. Appl. No. 13/074,439.

\* cited by examiner

COMPOSITION COMPRISING AN ACTIVE SUBSTANCE AND A POLYALKYLENEOXIDE VINYLESTER GRAFT POLYMER

The instant invention generally relates to a composition comprising an active substance and a polymeric additive. More specifically, the instant invention relates to a composition comprising a polymeric additive that is capable of increasing performance and/or stability of the active substance in the composition.

Compositions comprising an active substance are useful for many applications. One specific example of a useful composition is an agrochemical composition comprising a pesticide active ingredient as the active substance. In some instances, the agrochemical compositions are prepared by diluting the pesticide active ingredient with water, with the agrochemical compositions applied to plants to thereby deliver the pesticide active ingredient.

Performance and stability of compositions comprising the active substance is generally a concern, especially for the compositions that include pesticide active ingredients. Further, storage and temperature cycling prior to application generally exacerbate problems with stability of active substances in the compositions, and there is a constant desire to improve storage and freeze/thaw stability of active substances in such compositions to prevent separation between the active substances and the compositions.

Problems with stability of the active substances may be attributable to the fact that many active substances are capable of Ostwald ripening. Ostwald ripening is a phenomenon that leads to instability of some active substances in compositions. Although many active substances do not exhibit Ostwald ripening, Ostwald ripening can occur under some circumstances when the compositions contain a continuous aqueous phase and an active substance that is capable of transport through the continuous aqueous phase. Generally, Ostwald ripening proceeds through a mechanism in which smaller particles are incorporated into larger particles because larger particles are more energetically favored than smaller particles. Particle size growth due to Ostwald ripening commonly leads to instability of the active substance in the compositions because larger particles are generally more prone to settling out of the compositions.

Ostwald ripening is generally facilitated by dissolution of the active substances into the continuous aqueous phase, which can occur even if the solubility of the active substances in water is low. However, high solubility of the active substances in water increases the incidence of Ostwald ripening for active substances that are capable of Ostwald ripening. For this reason, and because many pesticide active ingredients are capable of Ostwald ripening, many water-based agrochemical compositions make use of pesticide active ingredients having a relatively low water solubility of less than 100 ppm in water.

It is known to use various additives to enhance stability of compositions, including compositions that include active substances capable of Ostwald ripening. Examples of such additives include poloxamers and industry benchmarks such as Morwet® D425 and the recently developed Atlox® 4913. Morwet® D425 is a naphthalene-sulfonate formaldehyde condensate and Atlox® 4913 is a graft polymer comprising a backbone of methyl methacrylate and methacrylic acid units and side chains of polyethylene glycol capped with methoxy groups. While Atlox® 4913 is widely used, efforts continue to develop novel additives that perform as well as or better than Atlox® 4913 for purposes of increasing the performance of and/or increasing the stability of the active substances included in the compositions. Improvements in inhibition of Ostwald ripening by novel additives could lead to the ability to use active substances that are more water soluble in the compositions while still enabling sufficient stability of the included in the compositions to be achieved.

Beside a high stability of compositions comprising the active substance, the high performance of the active substance is generally a concern, especially for the compositions that include pesticide active ingredients. In general, a high stability as well as a high performance should be achieved at the same time.

SUMMARY OF THE INVENTION AND ADVANTAGES

The instant invention provides a composition and a method of preparing the composition. The composition comprises an active substance and a polymeric additive. The polymeric additive comprises:

1) at least one unit represented by the formula (I):

wherein each R is independently selected from the group of a hydrogen atom, an alkyl group, an aryl group, and combinations thereof; and Z comprises at least 10 units represented by the formula (II):

wherein each $R^1$ is independently selected from the group of a hydrogen atom, an alkyl group, an aryl group, a carbonyl group, a hydroxyl group, an ether group, and combinations thereof; and $R^2$ is a $C_1$-$C_{10}$ hydrocarbon group; and 2) at least one unit represented by the formula (III):

wherein A is an alkyleneoxy group having from 2 to 10 carbon atoms.

The method of preparing the composition comprises the step of combining the active substance and the polymeric additive to form the composition.

The composition of the instant invention exhibits excellent performance and stability. In fact, the performance and stability of the composition is comparable to performance and stability achieved when the benchmarks additives Morwet® D425 or Atlox® 4913 are used, with superior results achieved under certain circumstances.

DETAILED DESCRIPTION OF THE INVENTION

A composition and a method of preparing the composition are provided. The composition comprises an active substance and a polymeric additive.

The active substance typically includes, but is not limited to, biologically active substances, i.e., those having an adverse or beneficial effect on living matter. As described in further detail below, the active substance may also include any substance capable of transport through a continuous aqueous phase to thereby result in Ostwald ripening. However, it is to be appreciated that the active substance is not limited to substances that are biologically active or to substances capable of transport through a continuous aqueous phase. The active substance may be in liquid or in solid particle form. Additionally, the active substance may be water-soluble, water-insoluble, partially water-soluble, oil-soluble, oil-insoluble, and combinations thereof. An example of an active substance that is partially water-soluble includes, but is not limited to, an active substance having low solubility in water of up to 500 ppm at temperatures of from −15° Celsius to 54° Celsius. It is to be appreciated that the composition may include a combination of active substances that are generally described above. In one embodiment, the active substance may comprise solid particles of a partially water-soluble pesticide active ingredient. In another embodiment, the active substance may comprise a liquid pesticide active ingredient that is both oil-soluble and water-insoluble. In embodiments wherein the active substance comprises a pesticide active ingredient, the composition may be used to treat plants by applying the composition to the plants. In another embodiment, the present invention relates to a method for controlling phytopathogenic fungi and/or undesired plant growth and/or undesired attack by insects or mites and/or for regulating the growth of plants, where the composition according to the invention is allowed to act on the particular pests, their habitat or the plants to be protected from the particular pest, the soil and/or on undesired plants and/or the useful plants and/or their habitat. In a preferred embodiment, the active substance is a pesticide active ingredient (also called pesticide). The term pesticides refers to at least one pesticide selected from the group of the fungicides, insecticides, nematicides, herbicides, safeners and/or growth regulators. Preferred pesticides are fungicides, insecticides, herbidides and growth regulators. Especially preferred pesticides are fungicides. Mixtures of pesticides of two or more of the abovementioned classes may also be used. The skilled worker is familiar with such pesticides, which can be found, for example, in the Pesticide Manual, 14th Ed. (2006), The British Crop Protection Council, London. Examples of suitable pesticides are:

A) Strobilurins
- azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, 2-[2-(2,5-dimethyl-phenoxymethyl)-phenyl]-3-methoxy-acrylic acid methyl ester and 2 (2-(3-(2,6-dichlorophenyl)-1-methyl-allylideneaminooxymethyl)-phenyl)-2-methoxyimino-N methyl-acetamide;

B) Carboxamides
- carboxanilides: benalaxyl, benalaxyl-M, benodanil, bixafen, boscalid, carboxin, fenfuram, fenhexamid, flutolanil, fluxapyroxad, furametpyr, isopyrazam, isotianil, kiralaxyl, mepronil, metalaxyl, metalaxyl-M (mefenoxam), ofurace, oxadixyl, oxycarboxin, penflufen, penthiopyrad, sedaxane, tecloftalam, thifluzamide, tiadinil, 2-amino-4 methyl-thiazole-5-carboxanilide, N-(4'-trifluoromethylthiobiphenyl-2-yl)-3 difluoromethyl-1-methyl-1H pyrazole-4-carboxamide and N-(2-(1,3,3-trimethyl-butyl)-phenyl)-1,3-dimethyl-5 fluoro-1H-pyrazole-4 carboxamide;
- carboxylic morpholides: dimethomorph, flumorph, pyrimorph;
- benzoic acid amides: flumetover, fluopicolide, fluopyram, zoxamide;
- other carboxamides: carpropamid, dicyclomet, mandipropamid, oxytetracyclin, silthiofam and N-(6-methoxy-pyridin-3-yl)cyclopropanecarboxylic acid amide;

C) Azoles
- triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole;
- imidazoles: cyazofamid, imazalil, pefurazoate, prochloraz, triflumizol;
- benzimidazoles: benomyl, carbendazim, fuberidazole, thiabendazole;
- others: ethaboxam, etridiazole, hymexazole and 2-(4-chloro-phenyl)-N-[4-(3,4-dimethoxy-phenyl)-isoxazol-5-yl]-2-prop-2-ynyloxy-acetamide;

D) Heterocyclic Compounds
- pyridines: fluazinam, pyrifenox, 3-[5-(4-chloro-phenyl)-2,3-dimethyl-isoxazolidin-3 yl]-pyridine, 3-[5-(4-methyl-phenyl)-2,3-dimethyl-isoxazolidin-3-yl]-pyridine;
- pyrimidines: bupirimate, cyprodinil, diflumetorim, fenarimol, ferimzone, mepanipyrim, nitrapyrin, nuarimol, pyrimethanil;
- piperazines: triforine;
- pyrroles: fenpiclonil, fludioxonil;
- morpholines: aldimorph, dodemorph, dodemorph-acetate, fenpropimorph, tridemorph;
- piperidines: fenpropidin;
- dicarboximides: fluoroimid, iprodione, procymidone, vinclozolin;
- non-aromatic 5-membered heterocycles: famoxadone, fenamidone, flutianil, octhilinone, probenazole, 5-amino-2-isopropyl-3-oxo-4-ortho-tolyl-2,3-dihydro-pyrazole-1 carbothioic acid S-allyl ester;
- others: acibenzolar-S-methyl, ametoctradin, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propyl-chromen-4-one, 5-chloro-1 (4,6-dimethoxy-pyrimidin-2-yl)-2-methyl-1H-benzoimidazole and 5 chloro-7 (4-methylpiperidin-1-yl)-6-(2,4,6-trifluorophenyl)-[1,2,4]triazolo[1,5 a]pyrimidine;

E) Carbamates
- thio- and dithiocarbamates: ferbam, mancozeb, maneb, metam, methasulphocarb, metiram, propineb, thiram, zineb, ziram;
- carbamates: benthiavalicarb, diethofencarb, iprovalicarb, propamocarb, propamocarb hydro-chlorid, valifenalate and N-(1-(1-(4-cyano-phenyl)ethanesulfonyl)-but-2-yl) carbamic acid-(4-fluorophenyl) ester;

F) Other Active Substances guanidines: guanidine, dodine, dodine free base, guazatine, guazatine-acetate, iminoctadine, iminoctadine-triacetate, iminoctadine-tris(albesilate);

antibiotics: kasugamycin, kasugamycin hydrochloride-hydrate, streptomycin, polyoxine, validamycin A;

nitrophenyl derivates: binapacryl, dicloran, dinobuton, dinocap, nitrothal-isopropyl, tecnazen, organometal compounds: fentin salts, such as fentin-acetate, fentin chloride or fentin hydroxyide;

sulfur-containing heterocyclyl compounds: dithianon, isoprothiolane;

organophosphorus compounds: edifenphos, fosetyl, fosetyl-aluminum, iprobenfos, phosphorous acid and its salts, pyrazophos, tolclofos-methyl;

organochlorine compounds: chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitro-phenyl)-N-ethyl-4-methyl-benzenesulfonamide;

inorganic active substances: Bordeaux mixture, copper acetate, copper hydroxide, copper oxychloride, basic copper sulfate, sulfur;

antifungal biocontrol agents, plant bioactivators: Ampelomyces quisqualis (e.g. AQ 10® from Intrachem Bio GmbH & Co. KG, Germany), *Aspergillus flavus* (e.g. AFLAGUARD® from Syngenta, CH), *Aureobasidium pullulans* (e.g. BOTECTOR® from bio-ferm GmbH, Germany), *Bacillus pumilius* (e.g. isolate NRRL-Nr. B-21661 in RHAPSODY®, SERENADE® MAX and SERENADE® ASO from Fa. AgraQuest Inc., USA), *Bacillus subtilis* var. *amyloliquefa-ciens* FZB24 (e.g. TAEGRO® from Novozyme Biologicals, Inc., USA), *Candida oleophila* I-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Cryphonectria parasitica* (e.g. *Endothia parasitica* from CNICM, France), *Cryptococcus albidus* (e.g. YIELD PLUS® from Anchor Bio-Technologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone Biolnnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REME-DIER® WP from Isagro Ricerca, Italy), *T. polysporum* and *T. harzianum* (e.g. BINAB® from BINAB Bio-Innovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy), *Ulocladium oudemansii* HRU3 (e.g. BOTRY-ZEN® from Botry-Zen Ltd, NZ);

others: biphenyl, bronopol, cyflufenamid, cymoxanil, diphenylamin, metrafenone, pyriofenone, mildiomycin, oxin-copper, prohexadione-calcium, spiroxamine, tebufloquin, tolylfluanid, N-(cyclopropylmethoxy-imino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N methyl formamidine, N' (4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2 methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dimethyl-quinolin-4-yl ester and N-Methyl-2-{1-[(5-methyl-3-trifluoromethyl-1H-pyrazol-1-O-acetyl]-piperidin-4-yl}-N-[(1R)-1,2,3,4-tetrahydronaphthalen-1-yl]-4-thiazole-carboxamide.

G) Growth Regulators abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6 benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole;

H) Herbicides acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;

amino acid derivatives: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

Bipyridyls: diquat, paraquat;

(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;
cyclohexanediones: butroxydim, clethodim, cycloxydim, profoxydim, sethoxydim, tepraloxydim, tralkoxydim;
dinitroanilines: benfluralin, ethalfluralin, oryzalin, pendimethalin, prodiamine, trifluralin;
diphenyl ethers: acifluorfen, aclonifen, bifenox, diclofop, ethoxyfen, fomesafen, lactofen, oxyfluorfen;
hydroxybenzonitriles: bomoxynil, dichlobenil, ioxynil;
imidazolinones: imazamethabenz, imazamox, imazapic, imazapyr, imazaquin, imazethapyr;
phenoxy acetic acids: clomeprop, 2,4-dichlorophenoxyacetic acid (2,4-D), 2,4-DB, dichlorprop, MCPA, MCPA-thioethyl, MCPB, Mecoprop;
pyrazines: chloridazon, flufenpyr-ethyl, fluthiacet, norflurazon, pyridate;
pyridines: aminopyralid, clopyralid, diflufenican, dithiopyr, fluridone, fluoroxypyr, picloram, picolinafen, thiazopyr;
sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1 ((2-chloro-6-propyl-imidazo[1,2-b]pyridazin-3-ypsulfonyl)-3-(4,6-dimethoxy-pyrimidin-2-yl)urea;
triazines: ametryn, atrazine, cyanazine, dimethametryn, ethiozin, hexazinone, metamitron, metribuzin, prometryn, simazine, terbuthylazine, terbutryn, triaziflam;
ureas: chlorotoluron, daimuron, diuron, fluometuron, isoproturon, linuron, methabenzthiazuron, tebuthiuron;
other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;
others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethlyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, fluorochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

I) Insecticides
organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;
carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;
pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;
insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;
nicotinic receptor agonists/antagonists compounds: clothianidin, dinotefuran, imidacloprid, thiamethoxam, nitenpyram, acetamiprid, thiacloprid, 1-(2-chloro-thiazol-5-ylmethyl)-2-nitrimino-3,5-dimethyl-[1,3,5]triazinane;
GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H pyrazole-3-carbothioic acid amide;
macrocyclic lactone insecticides: abamectin, emamectin, milbemectin, lepimectin, spinosad, spinetoram;
mitochondrial electron transport inhibitor (METI) I acaricides: fenazaquin, pyridaben, tebufenpyrad, tolfenpyrad, flufenerim;
METI II and III compounds: acequinocyl, fluacyprim, hydramethylnon;
Uncouplers: chlorfenapyr;
oxidative phosphorylation inhibitors: cyhexatin, diafenthiuron, fenbutatin oxide, propargite;
moulting disruptor compounds: cryomazine;
mixed function oxidase inhibitors: piperonyl butoxide;
sodium channel blockers: indoxacarb, metaflumizone;
others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluoron, and pyrifluquinazon.

In preferred embodiment, the pesticide has a solubility in water of less than 10 g/l at 20° C., more preferably of less than 1 g/l, even more preferably of less than 0,5 g/l, and most preferably of less than 0,1 g/l.

Examples of suitable pesticide active ingredients, for purposes of the instant invention, include but are not limited to atrazine, 3-(3,4-dichlorophenyl)-1,1-dimethylurea (commonly referred to by the tradename Diuron®), carbaryl, tebuconazole, chlorothalonil, copper oxychloride, carbendazim, and metolachlor. More preferred pesticides are difenoconazole, metrafenone, and a mixture of difenoconazole and metrafenone. The total amount of all active substance(s) present in the composition is typically up to 60 percent by weight, alternatively from 10 to 50 percent by weight, alternatively from 20 to 50 percent by weight, based on the total weight of the composition. In this regard, the composition may include relatively high amounts of the active substance(s) as compared to formulations that are intended for end user use.

The composition further comprises a polymeric additive. The benefits associated with the polymeric additive are typically pronounced in compositions having high amounts of the active substance(s); however, the benefits associated with the polymeric additive are also realized in compositions having low amounts of the active substance(s). The polymeric additive has at least one unit represented by the formula (I):

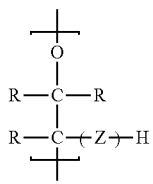

(I)

wherein each R is independently selected from the group of a hydrogen atom, an alkyl group, an aryl group, and combinations thereof; and Z comprises at least 10 units represented by the formula (II):

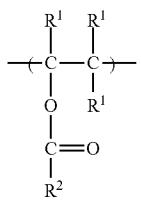

(II)

wherein each $R^1$ is independently selected from the group of a hydrogen atom, an alkyl group, an aryl group, a carbonyl group, a hydroxyl group, an ether group, and combinations thereof; and $R^2$ is a $C_1$-$C_{10}$ hydrocarbon group. It is to be appreciated that, when present, the alkyl and/or aryl groups of R and/or $R^1$ may be monovalent.

Preferably, each R is independently selected from the group of a hydrogen atom, a $C_1$ to $C_5$ alkyl group, and combinations thereof. More preferably, each R is independently selected from the group of a hydrogen atom, a methyl group, and combinations thereof. Especially preferred is R a hydrogen atom.

Preferably, $R^1$ is independently selected from the group of a hydrogen atom, an alkyl group, and combinations thereof. More preferably is $R^1$ a hydrogen atom. $R^2$ is preferably a $C_1$-$C_5$ hydrocarbon group. $R^2$ is more preferably a methyl group.

In a preferred embodiment, R is independently selected from the group of a hydrogen atom, a $C_1$ to $C_5$ alkyl group, and combinations thereof, $R^1$ is a hydrogen atom, and $R^2$ is a methyl group.

Typically, the number of units represented by the formula (II) that may be present in Z is from 10 to 200, alternatively from 20 to 100, alternatively from 30 to 70, and alternatively from 40 to 60, units. Typically, the unit represented by the formula (II) is present in an amount of from 45% to 75% by weight and alternatively from 55% to 65% by weight, based on the total weight of the polymeric additive.

In one embodiment, Z further comprises at least one unit represented by the formula (IV):

(IV)

wherein each $R^3$ is independently selected from the group of a hydrogen atom, an alkyl group, an aryl group, a carbonyl group, a hydroxyl group, an ether group, and combinations thereof; and wherein $R^3$ is not an ester group. When present, the number of units represented by the formula (IV) that may be present in Z is from 10 to 200, alternatively from 20 to 100, and alternatively from 30 to 70. It is contemplated that units represented by the formula (II), and when present the formula (IV), may be distributed randomly or blockwise within Z. Preferably, Z comprises up to 20 mol % units of the formula (VI), more preferably up to 5 mol %, and especially up to 0,5 mol %.

Typically, the number of units represented by the formula (I) that are present in the polymeric additive is from 1 to 30, alternatively from 1 to 15, and alternatively from 3 to 10, units represented by the formula (I).

When the polymeric additive has at least two units represented by the formula (I), the polymeric additive may be referred to as a "comb" polymer due to the structure thereof. It is contemplated that, when the polymeric additive has at least two units represented by the formula (I), each unit may be distributed randomly or regularly along a polyether backbone.

The polymeric additive further includes at least one unit represented by the formula (III):

(III)

wherein A is an alkyleneoxy group having from 2 to 10 carbon atoms, preferably from 2 to 5, and especially from 2 to 3 carbon atoms. A may independently represent the same or different alkyleneoxy groups having from 2 to 10 carbon atoms. Examples of suitable alkyleneoxy groups include, but are not limited to, ethylene oxide, propylene oxide, butylene oxide, decene oxide, and styrene oxide. It is contemplated that, when A represents different alkyleneoxy groups, the different alkyleneoxy groups may be distributed randomly or blockwise within the polyether backbone. In one embodiment, A represents the same alkyleneoxy group and A is ethylene oxide. When present, the number of units represented by the formula (III) that may be present in the polymeric additive is from 10 to 150 and alternatively from 25 to 80.

The number of units represented by the formula (I) and when present the formula (III) substantially control chain length in the polymeric additive. Furthermore, the number of units represented by the formula (I) and the formula (III), as well as the number of units present in Z and the number of units represented by the formula (IV), substantially control a number average molecular weight of the polymeric additive. In one embodiment, the polymeric additive has a molecular weight Mn of from 5,000 to 200,000 g/mol and alternatively from 15,000 to 50,000 g/mol. The polymeric additive may be terminated by hydroxy groups or alkylated on one or both terminal OH groups. Suitable alkyl radicals are branched or unbranched $C_1$- to $C_{22}$-alkyl radicals. Preferably, the polymeric additive is terminated by hydroxy groups.

In a preferred embodiment, the polymeric additive comprises
1) at least one unit represented by the formula (I), wherein each R is independently selected from the group of a hydrogen atom, an alkyl group, and combinations thereof; and
    Z comprises at least 10 units represented by the formula (II), wherein each $R^1$ is a hydrogen atom; and $R^2$ is a $C_1$-$C_5$ hydrocarbon group; and
2) at least one unit represented by the formula (III), wherein A is an alkyleneoxy group having from 2 to 3 carbon atoms.

In a more preferred embodiment, the polymeric additive comprises
1) at least one unit represented by the formula (I), wherein each R is a hydrogen atom; and
    Z comprises at least 10 units represented by the formula (II), wherein each $R^1$ is a hydrogen atom; and $R^2$ is a methyl; and
2) at least one unit represented by the formula (III), wherein A is an alkyleneoxy group having 2 carbon atoms.

The polymeric additive is obtainable by well known methods for graft polymerization. An advantageous process is for example given in WO 2007/138053, page 5, line 14 to page 10, line 25. The polymeric additive is typically present in the composition in an amount of at least 0.5 percent by weight based on the total weight of the composition. Alternatively, the polymeric additive is present in the composition in an amount of from 0.5 to 10.0, alternatively from 0.5 to 5, and alternatively from 1 to 3 percent by weight, based on the total weight of the composition. In a further preferred embodiment, the amount of the polymeric additive is usually in the range of from 5 to 1000 wt %, preferably from 10 to 500 wt %, more preferably from 20 to 100 wt %, based on the weight of the active substance.

Without being bound to any particular theory, it is believed that the polymeric additive increases performance and/or increases the stability of the active substance included in the composition depending on the particular active substance(s) included in the composition. More specifically, it is believed that the polymeric additive increases stability of the active substance by wrapping around the active substance. As discussed in greater detail below, the polymeric additive is particularly effective at stabilizing any active substance(s) capable of transport through a continuous aqueous phase to thereby result in Ostwald ripening.

The composition can also comprise additional components other than the active substance and the polymeric additive. For example, the composition may include wetting agents; surfactants; emulsifiers; antifreeze for purposes of improving freeze/thaw stability of the composition; antifoams; anti-settling agents such as xanthan gum; biocides; and combinations of the aforementioned additives. However, it is to be appreciated that the wetting agents, the surfactants, and the emulsifiers are optional. Examples of suitable wetting agents include those selected from the group of alcohol alkoxylates, polyalkylene glycol ethers, naphthalene-sulfonate formaldehyde condensates, and combinations thereof. Examples of an alcohol alkoxylate include, but are not limited to, Lutensol® XL and Lutensol® XP products commercially available from BASF Corporation. An example of a polyalkylene glycol ether includes, but is not limited to, Pluriol® WSB 125 commercially available from BASF Corporation. An example of a naphthalene-sulfonate formaldehyde condensate is Morwet® D425 commercially available from AkzoNobel. While Morwet® D425 is a known additive, it can also be included for its known wetting properties as well. In the context of the instant invention, Morwet® D425 may be included primarily as a wetting agent. In an embodiment where the composition further comprises the wetting agent, the wetting agent may be present in an amount of from 1 percent to 20 percent by weight, based on the total weight of the composition. Alternatively, the wetting agent may be present in an amount of from 1 to 10, more typically 1 to 5, and most typically 2 to 4 percent based on the total weight of the composition. Examples of suitable surfactants may include anionic surfactants such as calcium dodecylbenzenesulfonate. Examples of suitable emulsifiers may include nonionic emulsifiers such as alcohol alkoxylates as described above. Typically, the additional components are present in an amount of up to 20 percent by weight and more typically up to 15 percent by weight, based on the total weight of the composition.

The active substance may also be diluted with a solvent component to form the composition. The solvent component may include water, water-miscible liquids, oils, oil-miscible liquids, propylene glycol, tripropylene glycol, acetaldehyde, other known carriers, and combinations thereof. In one embodiment, more water and water-miscible constituents are present than oils and oil-miscible constituents. Under such circumstances, the solvent component may comprise a continuous aqueous phase. When included, the solvent component is typically present in the composition in an amount of from 10 to 75 percent by weight, alternatively from 10 to 60 percent by weight, alternatively from 20 to 50 percent by weight, alternatively from 30 to 40 percent by weight, based on the total weight of the composition.

In a preferred embodiment, the actice substance is a pesticide and the composition according to the invention is a agrochemical composition. This agrochemical compositions may also comprise auxiliaries which are customary in agrochemical compositions. The auxiliaries used depend on the particular application form and active substance, respectively. Examples for suitable auxiliaries are solvents, solid carriers, dispersants or emulsifiers (such as further solubilizers, protective col-loids, surfactants and adhesion agents), organic and anorganic thickeners, bacteri-cides, anti-freezing agents or anti-foaming agents.

Suitable solvents for agrochemical compositions are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e.g. amines such as N-methylpyrrolidone. In a preferred embodiement, the solvent comprises water. The water content of the agrochemical composition is preferably at least 10 wt %, more preferably at least 25 wt %, and most preferably at least 35 wt %, based on the total weight of the composition. The composition may comprise up to 80 wt % of water.

Suitable surfactants for agrochemical compositions (adjuvants, wtters, tackifiers, dispersants or emulsifiers) are alkali metal, alkaline earth metal and ammonium salts of aromatic sulfonic acids, such as ligninsulfonic acid (Borresperse® types, Borregard, Norway) phenolsulfonic acid, naph-thalenesulfonic acid (Morwet® types, Akzo Nobel, U.S.A.), dibutylnaphthalene-sulfonic acid (Nekal® types, BASF, Germany), and fatty acids, alkylsulfonates, alkylarylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e.g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers thereof.

Examples for thickeners for agrochemical compositions (i.e. compounds that impart a modified flowability to com-posi-tions, i.e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA). Bactericides for agrochemical compositions may be added for preservation and stabilization of the composition. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie). Examples for suitable anti-freezing agents for agrochemical compositions are ethylene glycol, propylene glycol, urea and glycerin. Examples for anti-foaming agents for agro-chemical compositions are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof.

The agrochemical composition, which comprises a pesticide as active substance, may be present in any known formulation type for agrochemical compositions, e.g. solutions, emulsions, suspensions, dusts, powders, pastes and granules. Preferably, the agrochemical composition is a suspension. The formulation type depends on the particular intended purpose; in each case, it should ensure a fine and uniform distribution of the compound according to the invention. Examples for formulation types are suspensions (SC, OD, FS), emulsifiable concentrates (EC), emulsions (EW, EO, ES), pastes, pastilles, wettable powders or dusts (WP, SP, SS, WS, DP, DS) or granules (GR, FG, GG, MG), which can be water-soluble or wettable, as well as gel formulations for the treatment of plant propagation materials such as seeds (GF). Usually the formulation types (e.g. SC, OD, FS, EC, WG, SG, WP, SP, SS, WS, GF) are employed diluted. Composition types such as DP, DS, GR, FG, GG and MG are usually used undiluted. Preferred formulation types are suspensions, e.g. SC.

The agrochemical compositions generally comprise between 0.01 and 95%, preferably between 0.1 and 90%, most preferably between 0.5 and 90%, by weight of pesticide. The pesticides are employed in a purity of from 90% to 100%, preferably from 95% to 100% (according to NMR spectrum).

In a preferred embodiment, the agrochemical composition is a dispersion (e.g. emulsion or suspension, or suspoemulsion), preferably a suspension. More preferably, the agrochemical composition is an aqueous dispersion, such as an aqueous suspension. The pesticide may be present in any form, such as solid, liquid or dissolved. Preferably the pesticide is present in solid form, more preferably in form of solid particles, which are suspended in the composition. The average particle size of the suspended pesticide is typically at least 40% below 2,0 µm, preferably at least 55% as determined by dynamic light scattering.

The viscosity of a liquid agrochemical composition is usually up to 1000 mPas, preferably up to 700 mPas, more preferably up to 500 mPas, and especially up to 400 mPas (measured according to specifications of Food and Agricultural Organization (FAO) MT 192).

In a preferred embodiment, the composition according to the invention comprises metrafenone, difenoconazole, and a polymeric additive comprising
1) at least one unit represented by the formula (I), wherein each R is independently selected from the group of a hydrogen atom, an alkyl group, and combinations thereof; and
 Z comprises at least 10 units represented by the formula (II), wherein each $R^1$ is a hydrogen atom; and $R^2$ is a $C_1$-$C_5$ hydrocarbon group; and
2) at least one unit represented by the formula (III), wherein A is an alkyleneoxy group having from 2 to 3 carbon atoms.

In another preferred embodiment, the composition according to the invention is a dispersion (e.g. emulsionor, suspension, or suspoemulsion), which comprises a pesticide, and a polymeric additive comprising
1) at least one unit represented by the formula (I), wherein each R is independently selected from the group of a hydrogen atom, an alkyl group, and combinations thereof; and
 Z comprises at least 10 units represented by the formula (II), wherein each $R^1$ is a hydrogen atom; and $R^2$ is a $C_1$-$C_5$ hydrocarbon group; and
2) at least one unit represented by the formula (III), wherein A is an alkyleneoxy group having from 2 to 3 carbon atoms.

The present invention also relates to a use of the composition according to the invention, wherein the active substance is a pesticide, for enhancing the pesticidal activity of said pesticide. Preferably, the amount of the polymeric additive is in the range of from 10 to 500 wt %, based on the weight of the pesticide.

The present invention also relates to a use of the composition according to the invention, wherein the active substance is a pesticide, for enhancing the retention of said pesticide on plants.

Ostwald Ripening

In one embodiment, the active substance is in solid particle form and is capable of transport through a continuous aqueous phase, when present, to thereby result in Ostwald Ripening. The active substance that is capable of Ostwald ripening is herein after referred to as the "O.R. substance". In one specific embodiment, the composition includes the O.R. substance, a solvent component comprising a continuous aqueous phase to dilute the O.R. substance, and the polymeric additive. This particular embodiment of the composition is herein after referred to as a "suspension composition" and will be described in greater detail below. It is to be appreciated that oils and oil-miscible components may also be present in which case the composition may technically be referred to as a suspoemulsion. However, for simplicity, "suspension composition" refers to suspensions and suspoemulsions.

As discussed above, the O.R. substance can include any substance that is capable of transport through a continuous aqueous phase thereby resulting in Ostwald ripening of the O.R. substance in the suspension composition. Ostwald ripening is a thermodynamically-driven spontaneous process wherein particles dispersed in a fluid change in size over time. Specifically, larger particles are more energetically favored than smaller particles. As a result, surface molecules detach from the smaller particles, are generally transported through the fluid by diffusion, and are incorporated into the larger particles. As the larger particles further increase in size over time, the incidence of the particles settling out of the fluid increases. Ostwald ripening can be readily observed by measuring differences in particle size over time for a given suspension composition. For purposes of the instant application, a substance that is capable of Ostwald ripening exhibits an increase in mean particle size of the substance of at least 0.1 micrometers after storage of a suspension composition at a temperature of 40° Celsius for a period of 28 days or after freeze-thaw cycling of the suspension composition for 7 days at temperatures ranging from −15° Celsius to +5° Celsius. It is to be appreciated that increased temperatures can increase the occurrence of Ostwald ripening.

Typically, the O.R. substance in the suspension composition has a degree of solubility in the continuous aqueous phase. However, if the solubility of the O.R. substance in the continuous aqueous phase is too high molecules of the O.R. substance will travel through the continuous aqueous phase too rapidly. As a result, Ostwald ripening may be too high to control and the O.R. substance may settle out of the continuous aqueous phase even when the polymeric additive is included in the suspension composition. Accordingly, the O.R. substance is typically partially water-soluble and has low solubility in the continuous aqueous phase of up to 500 ppm, typically from 10 to 100 ppm at temperatures of from −15° Celsius to 54° Celsius. In some instances, the solubility of the O.R. substance in the continuous aqueous phase is from 100 ppm to 500 ppm. As described in further detail below, one particular advantage of the suspension composition of the instant invention is the ability to use O.R. substances that are soluble in the continuous aqueous phase in excess of 100 ppm, with limited Ostwald ripening experienced over time as compared to previously known suspension compositions.

The O.R. substance is typically present in the suspension composition as particles having a volume-weighted mean particle size of from 1.5 to 3.2 micrometers, alternatively from 1.5 to 2.8 micrometers as measured by a Mastersizer 2000® particle size analyzer. The O.R. substance is typically milled to an initial volume-weighted mean particle size of from 1.5 to 2.2 micrometers. Typically, the O.R. substance has a volume-weighted mean particle size distribution that is mono-modal. The term "mono-modal" refers to a collection of particles which have a single, clearly discernable maxima on a particle size distribution curve (volume percent on the Y-axis, and particle size on the X-axis). For purposes of the suspension composition described herein, the "single clearly discernable maxima" is typically located on the particle size distribution curve from 1.5 to 3.2 micrometers. Additionally, about 90% of the particles of the O.R. substance typically fall below a particle size of 3.8 micrometers. Further, the O.R. substance is typically free of particles having a particle size greater than 10 micrometers. It is to be appreciated that, due to the fact that the O.R. substance has a degree of solubility in the continuous aqueous phase, at least some of the O.R. substance may be dissolved within the suspension composition. Additionally, the O.R. substance is typically present in the suspension composition including the continuous aqueous phase in an amount of up to 60 percent by weight, alternatively from 30 to 55 percent by weight, alternatively from 40 to 50 percent by weight, based on the total weight of the suspension composition. In this regard, the suspension composition typically includes relatively high amounts of the O.R. substance as compared to formulations that are intended for end user use. For example, when the O.R. substance is a pesticide component comprising a pesticide active ingredient, the suspension composition having the O.R. substance present in the above amounts may be a suspension concentrate that is diluted with additional water to form water-based agrochemical compositions that are then applied by end users to plants. As discussed above, the suspension composition further comprises a polymeric additive as described above. Due to the high amount of the O.R. substance that is typically included in the suspension composition, and due to the relatively water-insoluble nature of the O.R. substance, the polymeric additive is included in the suspension composition for purposes of stabilizing the O.R. substance within the continuous aqueous phase of the suspension composition. The polymeric additive is typically included in suspension compositions having high amounts of the O.R. substance; however, the polymeric additive is also effective for stabilizing purposes in suspension compositions having low amounts of the O.R. substance. The polymeric additive performs as well as industry benchmark additives as determined through suspensibility tests that are described in detail below. The polymeric additive that is included in the suspension composition of the instant invention also inhibits or limits Ostwald ripening of the O.R. substance within the suspension composition as described in further detail below, and such inhibition of Ostwald ripening is more effective than performance of industry benchmark additives in some circumstances.

The polymeric additive is present in the suspension composition in an amount sufficient to limit Ostwald ripening of the O.R. substance in the suspension composition. For purposes of the instant application, Ostwald ripening of the O.R. substance is "limited" when a change in mean particle size of the O.R. substance is less than 1.2 micrometers after storage of the suspension composition at a temperature of 40° Celsius for a period of 28 days, or after freeze-thaw cycling of the suspension composition for 7 days at temperatures ranging from −15° Celsius to +5° Celsius. Typically, the polymeric additive is present in an amount of at least 0.5 percent by weight based on the total weight of all components present in the suspension composition, which is an amount sufficient to limit Ostwald ripening of the O.R.

substance in the suspension composition. Alternatively, the polymeric additive is present in the suspension composition in an amount of from 0.5 to 10.0, alternatively from 0.5 to 5.0, and alternatively from 1.0 to 3.0 percent by weight, based on the total weight of the suspension composition.

It is to be appreciated that the polymeric additive described herein provides sufficiently acceptable suspensibility properties to the suspension composition, and sufficiently prevents Ostwald ripening, such that additional anti-settling agents (described above as additional components that may be present) are not required in many circumstances. However, depending upon the particular active substance that is included in the suspension composition, the anti-settling agent may be included in the suspension compositions to further stabilize the suspension composition.

In one specific embodiment, the suspension composition includes a solvent component comprising a continuous aqueous phase in an amount of from 10.0 to 60.0 percent by weight, the O.R. substance in an amount of up to 60.0 percent by weight, the polymeric additive in an amount of at least 0.5 percent, a wetting agent in an amount of from 1.0 to 20.0 percent, and additional components in an amount of up to 20.0 percent by weight, all based on the total weight of the suspension composition.

In another specific embodiment, the suspension composition includes a solvent component comprising a continuous aqueous phase in an amount of from 30 to 40 percent by weight, the O.R. substance in an amount of from 40 to 50 percent by weight, the polymeric additive in an amount of from 1 to 3 percent, a wetting agent in an amount of from 2 to 4 percent, and additional components in an amount of up to 15 percent by weight, all based on the total weight of the suspension composition.

In yet another specific embodiment, the suspension composition includes a solvent component comprising a continuous aqueous phase and an oil in an amount of from 18 to 72 percent by weight, the O.R. substance in an amount of from 5 to 30 percent by weight, a second active substance that is oil-soluble in an amount of from 5 to 30 percent by weight, the polymeric additive in an amount of from 1 to 5 percent by weight, a wetting agent in an amount of 1 to 5 percent, an emulsifier in an amount of 3 to 7 percent by weight, and additional components in an amount of up to 20 percent by weight; all based on the total weight of the suspension composition.

In still another specific embodiment, the suspension composition includes a solvent component comprising a continuous aqueous phase and an oil in an amount of from 18 to 72 percent by weight, the O.R. substance in an amount of from 15 to 25 percent by weight, a second active substance that is oil-soluble in an amount of from 15 to 25 percent by weight, the polymeric additive in an amount of from 2 to 4 percent by weight, a wetting agent in an amount of 2 to 3 percent, an emulsifier in an amount of 4 to 6 percent by weight, and additional components in an amount of up to 15 percent by weight; all based on the total weight of the suspension composition.

As described above, by including the specific polymeric additive in the suspension composition, diminished Ostwald ripening over time is experienced with the O.R. substance in the suspension composition as compared to when other additives are used. Without being bound to any particular theory, it is believed that the polyether backbone enables the polymeric additive to wrap around molecules and/or particles of the active substance thereby resulting in diminished Ostwald ripening over time of the active substance. Further, such performance with regard to inhibiting Ostwald ripening enables active substances that have higher water solubility than is currently acceptable to be used in the suspension composition. In particular, a change in mean particle size of the O.R. substance is typically less than 2.0 and more typically less than 1.2 micrometers after storage of the suspension composition at a temperature of 40° Celsius for a period of 28 days or after freeze-thaw cycling of the suspension composition for 7 days at temperatures ranging from −15° Celsius to +5° Celsius.

Method of Preparing the Composition

One method of preparing a composition in accordance with the instant invention comprises the step of combining the active substance and the polymeric additive in a vessel to form the composition. In one embodiment, the step of combining may further comprise combining the solvent component in the vessel to form the composition. In another embodiment, the step of combining may further comprise the step of combining a grinding media with at least one of the active substance and/or the polymeric additive in the vessel to form the composition. Grinding media are known in the art. In another embodiment, the step of combining may further comprise the step of combining the wetting agent with at least one of the active substance and/or the polymeric additive in the vessel to form the composition. Alternatively, the step of combining may further comprise the step of combining the grinding media and the wetting agent with at least one of the active substance and/or the polymeric additive in the vessel to form the composition. The vessel is typically a bead chamber of an Eiger mill; however, the vessel may alternatively be a mixing vessel of an attritor such as a Union Process Attritor system. The method may further comprise the step of decreasing a size of the active substance, typically through milling, to a volume-weighted average particle size of from 1.5 to 2.0 micrometers. The step of decreasing the size of the active substance typically occurs after combining the active substance and the polymeric additive to form the composition. The composition is typically chilled during milling to prevent the active substance from decomposing or melting during milling.

To test the composition for deterring the incidence of Ostwald ripening, the composition may be stored at a temperature of 40° Celsius for a period of 28 days or the composition may undergo freeze-thaw cycling for 7 days at temperatures ranging from −15° Celsius to +5° Celsius, under which conditions a change in mean particle size of the active substance may be less than 1.2 micrometers after storage or freeze-thaw cycling of the composition under certain circumstances, which represents superior performance relative to Ostwald ripening of the active substance present in the composition as compared to performance of benchmark additives.

Advantages of the present invention are for example, that the composition has an excellent stability (e.g. regarding particle size, viscosity). The composition increases the pesticidal activity of the pesticides. This adjuvant effect is achieved without decrease in the stability of the composition. The polymeric additive has a very low phytotoxicity, which is especially important for the treatment of vegetables and fruits. The polymeric additive can easily produced in industrial scale for low costs. The polymeric additive increases the retention of pesticides on leafs (spray retention).

The following examples are meant to illustrate the invention and are not to be viewed in any way as limiting to the scope of the invention.

EXAMPLES

Preparation of Polymeric Additive A

Polyethylene glycol (0,44 kg, Mn 6000) was melted at 90° C. and 0.6 g of tert-butyl per-2-ethylhexanoate, dissolved in of tripropylene glycol, were added. 7,75 mol of vinyl acetate were added under stirring within 6 h (feed 1), as well as 7 g of tert-butyl peroxy-2-ethylhexanoate, dissolved in tripropylene glycol, within 6.5 h (feed 2), and also, beginning 3 h after the start of feed 1, 0,23 kg of an alkoxylated C10-alcohol within 3.5 h (feed 3) were metered in in parallel continuously with constant flow rates at a temperature of 90° C. After the end of feeds 2 and 3 and subsequent stirring at 90° C. for a further hour, 6 g of tert-butyl peroxy-2-ethylhexanoate, dissolved in tripropylene glycol, were added in 3 portions at 90° C. with further stirring for two hours in each case. A solids content of about 88% by weight was established by adding water. The resulting graft polymer (Polymeric additive A) had a K value of 17-19 (1 wt % polymer in aqueous sodium chloride (3 wt %) at 23° C.), Mw 36000, and Mn 20 000 (measured by gel permeation chromatography, PMMA standard).

Preparation of Compositions (Part I)

Compositions were prepared including the components set forth in Table 1 below, with all amounts listed as percent by weight based on the total weight of the respective composition.

TABLE 1

Composition of the examples according to the invention

| Component | Ex. 1 | Ex. 2 | Ex. 3 | Ex. 4 | Ex. 5 | Ex. 6 |
|---|---|---|---|---|---|---|
| Solvent Constituent A | 34.55 | 34.55 | 34.65 | 34.45 | 34.45 | 34.45 |
| Solvent Constituent B | 10.0 | 10.0 | 10.0 | 10.0 | 10.0 | 10.0 |
| Solvent Constituent C | 0.045 | 0.045 | 0.045 | 0.045 | 0.045 | 0.045 |
| Wetting Agent A | 3.5 | 3.5 | 3.5 | 3.5 | 3.5 | 3.5 |
| Wetting Agent B | 0.225 | 0.225 | 0.225 | 0.225 | 0.225 | 0.225 |
| Polymeric Additive A | 1.08 | 1.08 | 1.08 | 1.08 | 1.08 | 1.08 |
| Active substance 1 | 50.0 | 50.0 | 50.0 | — | — | — |
| Active substance 2 | — | — | — | 50.0 | 50.0 | 50.0 |
| Additional Comp. A | 0.5 | 0.5 | 0.5 | 0.5 | 0.5 | 0.5 |
| Additional Comp. B | 0.1 | 0.1 | — | 0.2 | 0.2 | 0.2 |
| Total | 100.0 | 100.0 | 100.0 | 100.0 | 100.0 | 100.0 |

| Component | Ex. 7 | Ex. 8 | Ex. 9 | Ex. 10 | Ex. 11 |
|---|---|---|---|---|---|
| Solvent Constituent A | 34.4 | 34.38 | 39.4 | 34.65 | 39.4 |
| Solvent Constituent B | 10.0 | 10.0 | 10.0 | 10.0 | 10.0 |
| Solvent Constituent C | 0.045 | 0.045 | 0.045 | 0.045 | 0.045 |
| Wetting Agent A | — | — | 3.5 | 3.5 | 3.5 |
| Wetting Agent B | 0.225 | 0.225 | 0.225 | 0.225 | 0.225 |
| Polymeric Additive A | 1.08 | 1.08 | 1.08 | 1.08 | 1.08 |
| Polymeric Additive D | 3.5 | 3.5 | — | — | — |
| Active substance 2 | 50.0 | 50.0 | — | — | — |
| Active substance 3 | — | — | 45.0 | 50.0 | 45.0 |
| Additional Component A | 0.5 | 0.5 | 0.5 | 0.5 | 0.5 |
| Additional Component B | 0.25 | 0.27 | 0.25 | — | 0.25 |
| Total | 100.0 | 100.0 | 100.0 | 100.0 | 100.0 |

Composition of the comparative examples (not according to the invention)

| Component | Comp. Ex. 1 | Comp. Ex. 2 | Comp. Ex. 3 | Comp. Ex. 4 | Comp Ex. 5 | Comp. Ex. 6 |
|---|---|---|---|---|---|---|
| Solvent Constituent A | 34.5 | 34.5 | 34.5 | 34.3 | 34.25 | 34.5 |
| Solvent Constituent B | 10.0 | 10.0 | 10.0 | 10.0 | 10.0 | 10. |
| Wetting Agent A | 3.5 | 3.5 | 3.5 | 3.5 | 3.5 | 3.5 |
| Polymeric Additive B | 1.5 | 1.5 | 1.5 | 1.5 | 1.5 | 1.5 |
| Active substance 1 | 50.0 | 50.0 | 50.0 | — | — | — |
| Active substance 2 | — | — | — | 50.0 | 50.0 | — |
| Active substance 3 | — | — | — | — | — | 50.0 |
| Additional Comp. A | 0.5 | 0.5 | 0.5 | 0.5 | 0.5 | 0.5 |
| Additional Comp. B | — | — | — | 0.2 | 0.25 | — |
| Total | 100.0 | 100.0 | 100.0 | 100.0 | 100.0 | 100.0 |

| Component | Comp Ex. 7 | Comp. Ex. 8 | Comp. Ex. 9 | Comp. Ex. 10 | Comp. Ex. 11 | Comp. Ex. 12 |
|---|---|---|---|---|---|---|
| Solvent Constituent A | 34.5 | 34.5 | 39.25 | 34.5 | 34.5 | 34.4 |
| Solvent Constituent B | 10.0 | 10.0 | 10.0 | 10.0 | 10.0 | 10.0 |
| Wetting Agent A | 3.5 | 3.5 | 3.5 | — | — | — |
| Polymeric Additive B | 1.5 | 1.5 | 1.5 | — | — | — |
| Polymeric Additive C | — | — | — | 2.0 | 2.0 | 1.5 |
| Polymeric Additive D | — | — | — | 3.0 | 3.0 | 3.5 |
| Active substance 1 | — | — | — | 50.0 | 50.0 | 50.0 |
| Active substance 3 | 50.0 | 50.0 | 45.0 | — | — | — |
| Additional Comp. A | 0.5 | 0.5 | 0.5 | 0.5 | 0.5 | 0.5 |
| Additional Comp. B | — | — | 0.25 | — | — | 0.1 |
| Total | 100.0 | 100.0 | 100.0 | 100.0 | 100.0 | 100.0 |

| Component | Comp. Ex. 13 | Comp. Ex. 14 | Comp. Ex. 15 | Comp Ex. 16 | Comp Ex. 17 | Comp. Ex. 18 |
|---|---|---|---|---|---|---|
| Solvent Constituent A | 34.4 | 34.5 | 34.3 | 34.3 | 34.3 | 34.5 |
| Solvent Constituent B | 10.0 | 10.0 | 10.0 | 10.0 | 10.0 | 10.0 |
| Polymeric Additive C | 1.5 | 1.5 | 1.5 | 1.5 | 1.5 | 1.5 |
| Polymeric Additive D | 3.5 | 3.5 | 3.5 | 3.5 | 3.5 | 3.5 |
| Active substance 1 | 50.0 | 50.0 | — | — | — | — |

TABLE 1-continued

| Component | | | | | | |
|---|---|---|---|---|---|---|
| Active substance 2 | — | — | 50.0 | 50.0 | 50.0 | — |
| Active substance 3 | — | — | — | — | — | 50.0 |
| Additional Comp. A | 0.5 | 0.5 | 0.5 | 0.5 | 0.5 | 0.5 |
| Additional Comp. B | 0.1 | — | 0.2 | 0.2 | 0.2 | — |
| Total | 100.0 | 100.0 | 100.0 | 100.0 | 100.0 | 100.0 |

| Component | Comp. Ex. 19 | Comp. Ex. 20 | Comp. Ex. 21 |
|---|---|---|---|
| Solvent Constituent A | 34.5 | 39.3 | 39.3 |
| Solvent Constituent B | 10.0 | 10.0 | 10.0 |
| Polymeric Additive C | 1.5 | 1.5 | 1.5 |
| Polymeric Additive D[1] | 3.5 | 3.5 | 3.5 |
| Active substance 3 | 50.0 | 45.0 | 45.0 |
| Additional Component A | 0.5 | 0.5 | 0.5 |
| Additional Component B | — | 0.2 | 0.2 |
| Total | 100.0 | 100.0 | 100.0 |

Solvent Constituent A is water.
Solvent Constituent B is 1,2-propylene glycol.
Solvent Constituent C is tripropylene glycol containing trace amounts of acetaldehyde.
Wetting Agent A is Pluriol ® WSB 125 from BASF Corp., a polyalkylene glycol ether.
Wetting Agent B is Lutensol ® XL 100 from BASF SE, an ethoxylated C10-Guerbet alcohol, degree of ethoxylation equals about 10.
Polymeric Additive A was prepared as described above.
Polymeric Additive B is Atlox ® 4913 from Uniquema, a comb polymer based on methyl methacrylate, methacrylic acid and methoxy polyethylene glycol methacrylate.
Polymeric Additive C is a difunctional block copolymer surfactant terminating in primary hydroxyl groups, commercially available from BASF Corporation.
Polymeric Additive D is Morwet ® D425 from Akzo Nobel, a sodium salt of an alkyl naphthalene sulfonate condensate.
Active substance 1 is atrazine (a herbicide).
Active substance 2 is 3-(3,4-dichlorophenyl)-1,1-dimethylurea (a herbicide, also known as DCMC).
Active substance 3 is carbaryl (an insecticide).
Additional Component A is an antifoaming agent.
Additional Component B is an anti-settling agent.

The compositions are prepared by first weighing the appropriate amount of Solvent Constituent A to be used for purposes of preparing the compositions and adding the Solvent Constituent A to a vessel. The appropriate amounts of the Polymeric Additive and Wetting Agent are then determined according to the values set forth in Table 1 and are added to the vessel. The contents of the vessel are then mixed until the Polymeric Additive and Wetting Agent are dispersed in Solvent Constituent A.

The active substance is then added to the vessel followed by mixing until the contents of the vessel appear uniform. The Additional Components, Solvent Constituent B, and Solvent Constituent C are then added to the vessel, the vessel is covered, and the contents of the vessel are mixed for 1 hour.

An Eiger Mini 50 Bead Mill comprising a bead chamber is then used to mill the contents of the vessel to form the composition. The bead chamber is chilled using a chiller system with a coolant comprising a 50/50 parts by volume water/propylene glycol mixture. To mill the contents of the vessel, zirconium grinding media having an average diameter of from 0.8 to 1.0 mm is included in the bead chamber in an amount of 80 mL. The chiller system is then used to chill the bead chamber to a temperature of from 5 to 10° Celsius. A diverter valve of the bead mill is then set to recirculate. The contents of the vessel are then added to the bead chamber and milling is commenced with the bead mill in recirculation mode, with care taken to ensure that a temperature of the contents of the bead chamber does not exceed 40° Celsius. Samples are periodically taken from the bead mill to measure particle size, until a volume weighted particle size of the samples is measured to be from 1.7 to 2.0 micrometers, with no particles larger than 10 micrometers. Achievement of the desired particle size indicates achievement of the composition, and the contents of the bead chamber (excluding the beads) are collected for testing.

Test of Freeze/Thaw Stability

For testing purposes, the compositions of the instant invention are subjected to freeze/thaw cycling and storage under conditions of elevated temperatures as follows: Freeze-thaw cycling of the composition is performed by repeated temperature cycling of a test sample of the composition from −15° Celsius to +5° Celsius. Each freeze-thaw cycle is 1 week in duration and includes 3.5 days of storage at −15° Celsius, followed by 3.5 days storage at +5° Celsius. After completing a minimum of 6 freeze/thaw cycles, the physical properties of the sample are evaluated and compared to initial measurements to determine effects that may adversely alter the useful handling and end use properties of the composition.

Test of Storage Under Conditions of Elevated Temperatures

Storage under conditions of elevated temperatures is performed by placing a sample of the composition in an oven held at a temperature of the surrounding air of either 40° Celsius or 54° Celsius, depending on the substance included in the composition, for a period of 28 days, after which time physical properties of the sample are evaluated and compared to initial measurements to determine effects that may adversely alter the useful handling and end use properties of the composition. It was found that compositions including carbaryl formed pastes after storage at 54° Celsius. Storage under conditions of elevated temperatures, for compositions including carbaryl, is performed by placing a sample of the composition in an oven held at a temperature of the surrounding air of 40° Celsius for a period of 28 days, after which time physical properties of the sample are evaluated and compared to initial measurements to determine effects that may adversely alter the useful handling and end use properties of the composition including carbaryl.

Measurement of Particle Size in the Compositions

Physical properties of the compositions are measured in accordance with the following procedures, with the physical properties measured initially after preparation of the compositions, after freeze/thaw cycling, and after storage under conditions of elevated temperatures as described above.

Samples of the composition are dispersed in deionized water and analyzed for particle size using a Malvern Mastersizer 2000 Particle Size Analyzer commercially available from Malvern Instruments, Southborough, Mass. The sample is dispersed using a small volume recirculator and operations are performed using a standard operating procedure (SOP) created specifically to include such sample parameters as refractive index, mixing speed, analysis time, and number of measurements. Analysis is based on spherical assumptions and results are reported in terms of a volume-weighted mean diameter (i.e., volume-weighted mean particle size). Results are based on an acquisition range of 0.02-2000 µm and on the average of two runs. Initial particle sizes for each of the Examples and Comparative Examples as described above are set forth in Table 3 below.

Particle sizes for each of the Examples and Comparative Examples as described above are set forth in Table 3 below after subjecting the Examples and Comparative Examples to freeze/thaw cycling as described above. The change in particle size after freeze/thaw cycling is indicative of Ostwald ripening occurring within the respective compositions.

TABLE 3

Results of freeze/thaw cycling (Particle size is given as Volume -Weighted Mean Particle Size)

| Component | Initial Particle Size [μm] | Final Particle Size [μm] | Change in particle size, % |
|---|---|---|---|
| Example 1 | 2.119 | 2.152 | 1.560 |
| Example 2 | 2.030 | 2.062 | 1.580 |
| Example 3 | 1.734 | 2.051 | 18.280 |
| Example 4 | 1.634 | 1.544 | −5.510 |
| Example 5 | 2.037 | 2.034 | −0.150 |
| Example 6 | 1.818 | 1.770 | −2.640 |
| Example 7 | 1.686 | Not Tested | Not Tested |
| Example 8 | 1.689 | Not Tested | Not Tested |
| Example 9 | 1.716 | 1.730 | 0.820 |
| Example 10 | 2.057 | 2.211 | 7.490 |
| Example 11 | 1.864 | 1.824 | −2.150 |
| Comparative Example 1 | 1.600 | 1.619 | 1.190 |
| Comparative Example 2 | 1.640 | 1.626 | −0.850 |
| Comparative Example 3 | 1.700 | 1.676 | −1.410 |
| Comparative Example 4 | 1.450 | 1.574 | 8.550 |
| Comparative Example 5 | 1.483 | 3.334 | 124.810 |
| Comparative Example 6 | 2.077 | 2.030 | −2.260 |
| Comparative Example 7 | 2.054 | 2.120 | 3.210 |
| Comparative Example 8 | 1.974 | 2.230 | 12.970 |
| Comparative Example 9 | 2.095 | 2.127 | 1.530 |
| Comparative Example 10 | 1.450 | 1.415 | −2.410 |
| Comparative Example 11 | 1.483 | 1.458 | −1.690 |
| Comparative Example 12 | 2.077 | 2.097 | 0.960 |
| Comparative Example 13 | 2.054 | 2.069 | 0.730 |
| Comparative Example 14 | 1.974 | 2.048 | 3.750 |
| Comparative Example 15 | 1.301 | 1.331 | 2.310 |
| Comparative Example 16 | 1.689 | 2.133 | 26.290 |
| Comparative Example 17 * | 1.883 | 1.779 | −5.52 |
| Comparative Example 18 | 1.518 | 42.100 | 2673.390 |
| Comparative Example 19 | 1.455 | 43.520 | 2891.070 |
| Comparative Example 20 | 1.661 | 1.675 | 0.840 |
| Comparative Example 21 | 1.631 | 2.110 | 29.370 |

* Comparative Example 17 was evaluated after 30 freeze/thaw cycles.

Statistical analysis for the increases in particle size after freeze/thaw cycling is performed using JMP 8 software. The results in the statistical analysis indicate that the differences in the volume-weighted mean particle sizes between the Examples and Comparative Examples are not statistically significant, thereby indicating that the polymeric additives used in the Examples are as effective as the additives used in the Comparative Examples.

Particle sizes for each of the Examples and Comparative Examples as described above are set forth in Table 4 below after subjecting the Examples and Comparative Examples to storage under conditions of elevated temperature as described above. The change in particle size after storage under conditions of elevated temperature is also indicative of Ostwald ripening occurring within the respective compositions.

TABLE 4

Results of storage under elevated temperature (Particle size is given as Volume - Weighted Mean Particle Size)

| Component | Initial Particle Size [μm] | Final Particle Size [μm] | Change in particle size, % |
|---|---|---|---|
| Example 1 | 2.119 | 2.364 | 11.560 |
| Example 2 | 2.030 | 2.390 | 17.730 |
| Example 3 | 1.734 | 2.350 | 35.520 |
| Example 4 | 1.634 | 2.068 | 26.560 |
| Example 5 | 2.037 | 2.601 | 27.690 |
| Example 6 | 1.818 | 2.340 | 28.710 |
| Example 7 | 1.686 | 2.260 | 34.050 |
| Example 8 | 1.689 | 2.247 | 33.040 |
| Example 9** | 1.716 | N/A | N/A |
| Example 10** | 2.057 | N/A | N/A |
| Example 11 | 1.864 | 3.015 | 61.750 |
| Comparative Example 1 | 1.600 | 1.741 | 8.810 |
| Comparative Example 2 | 1.640 | 1.798 | 9.630 |
| Comparative Example 3 | 1.700 | 1.873 | 10.180 |
| Comparative Example 4 | 1.450 | 3.081 | 112.480 |
| Comparative Example 5 | 1.483 | 3.340 | 125.220 |
| Comparative Example 6** | 2.077 | N/A | N/A |
| Comparative Example 7** | 2.054 | N/A | N/A |
| Comparative Example 8** | 1.974 | N/A | N/A |
| Comparative Example 9 | 2.095 | 2.570 | 22.670 |
| Comparative Example 10 | 1.450 | 1.757 | 21.170 |
| Comparative Example 11 | 1.483 | 1.788 | 20.570 |
| Comparative Example 12 | 2.077 | 2.327 | 12.040 |
| Comparative Example 13 | 2.054 | 2.282 | 11.100 |
| Comparative Example 14 | 1.974 | 2.331 | 18.090 |
| Comparative Example 15 | 1.301 | 1.765 | 35.660 |
| Comparative Example 16 | 1.689 | 2.133 | 26.290 |
| Comparative Example 17 | 1.883 | 2.241 | 19.010 |
| Comparative Example 18** | 1.518 | N/A | N/A |
| Comparative Example 19** | 1.455 | N/A | N/A |
| Comparative Example 20 | 1.661 | 2.505 | 50.810 |
| Comparative Example 21 | 1.631 | 104.470 | 6305.270 |

**Data is unavailable as the example formed a paste.

Statistical analysis for the increase in particle size after storage under conditions of elevated temperature is also performed using JMP 8 software. The results in the statistical analysis indicate that the differences in the volume-weighted mean particle sizes between Examples 1-11 and Comparative Examples 1-21 are not statistically significant where the active substance used is atrazine, thereby indicating that the polymeric additives used in these Examples are as effective as the additives used in the respective Comparative Examples. Where the active substance used is 3-(3,4-dichlorophenyl)-1,1-dimethylurea the results indicate that although Examples 1-11 have lower average particle size change than Comparative Examples 1-21, the difference in the volume-weighted mean particle sizes between Examples 1-11 and Comparative Examples 1-21 are not statistically significant, thereby indicating that the polymeric additives used in these Examples are as effective as the additives used in the respective Comparative Examples. Where the active substance used is carbaryl and a thickener is present, the results indicate that the differences in the volume-weighted mean particle sizes between Examples 1-11 and Comparative Examples 1-21 are not statistically significant, thereby indicating that the polymeric additives used in these Examples are as effective as the additives used in the respective Comparative Examples. However, where the active substance used is carbaryl and a thickener is not present, differences in the volume-weighted mean particle sizes between Examples 1-11 and Comparative Examples 18 and 19 indicate that statistically significant minimization of Ostwald ripening is achieved when the polymeric additives of the Examples are used instead of the additives in the Comparative Examples 18 and 19.

Suspensibility Test

To test for suspensibility of the compositions, 150 ml of standard hard water (containing hard water ions such as magnesium and calcium in an amount of 342 ppm with a molar ratio of calcium ions to magnesium ions of 2:1) is measured in a 250 ml beaker. A magnetic stirrer is placed in the beaker and the beaker is placed on a stir plate. Speed for the stir plate is set such that a vortex does not reach the stir bar.

5.00±0.10 grams of the composition is then weighed in a weight-boat and placed into the beaker. A timer is started immediately and set for 2 minutes, with stirrer speed adjusted after adding the sample of the composition to the beaker to ensure good mixing.

After 2 minutes of mixing, the beaker is removed from the stir plate. The magnetic stirrer is removed and rinsed using a wash bottle filled with standard hard water. The contents of the beaker are then poured into a 250 ml graduated cylinder and the beaker is rinsed with the rinsate added to the 250 ml graduated cylinder. The volume in the cylinder is brought up to 250 ml using standard hard water. The steps of emptying and rinsing the beaker are performed within 1 minute.

The 250 ml graduated cylinder is then sealed and inverted for 15 cycles at 2-3 seconds per cycle and is then allowed to stand undisturbed at ambient temperature for 30 minutes. 225 ml of the suspension is then withdrawn from the 250 ml graduated cylinder within 10-25 seconds using a pipette, always keeping the pipette tip only a few mm below the surface of the liquid in the 250 ml graduated cylinder, with care taken to minimize disturbance of the entire cylinder. The liquid withdrawn using the pipette is discarded.

A dry evaporating dish is weighed to the nearest 0.05 grams. The remaining 25 ml in the 250 ml graduated cylinder is swirled to suspend particles present therein, and the contents of the 250 ml graduated cylinder are poured into the evaporating dish. The 250 ml graduated cylinder is rinsed, with the rinsate added to the evaporating dish.

The evaporating dish is then placed in a drying oven and allowed to dry overnight. When the contents of the evaporating dish are dry, the evaporating dish is removed from the oven and allowed to sit at room temperature of 21° Celsius for 5 minutes. The evaporating dish is then weighed.

Suspensibility is then determined by subtracting the weight of the residue in the evaporating dish from the mass of solids in the initial sample of the composition, and then dividing the result by the weight of the residue in the evaporating dish (and multiplying by 100 to obtain a percentage). Suspensibility is determined both initially, after storage at either 40° Celsius for 28 days, and after freeze/thaw cycling, and the results are shown in Table 5 below.

TABLE 5

Results of suspensibility test

| Component | Initial Suspensibility, % | Final Suspensibility After Storage at 40° or 54° C. for 28 Days, % | Final Suspensibility After Freeze/Thaw Cycling, % |
|---|---|---|---|
| Example 1 | 99.3 | 99.4 | 97.6 |
| Example 2 | 102.9 | 102.2 | 98.6 |
| Example 3 | 100.9 | Not Tested | 100.6 |
| Example 4 | 99.5 | 100.2 | 101.7 |
| Example 5 | 105.4 | 97.2 | 98.8 |
| Example 6 | Not Tested | 100.1 | 99.7 |
| Example 7 | 98.1 | 94.2 | Not Tested |
| Example 8 | 101.3 | 98.4 | Not Tested |
| Example 9 | 92.9 | Not Tested | 100.1 |
| Example 10 | 98.0 | Not Tested | Not Tested |
| Comparative Example 1 | 101.7 | 97.8 | 101.7 |
| Comparative Example 2 | 101.0 | N/A | 99.3 |
| Comparative Example 3 | 99.4 | 96.3 | 104.1 |
| Comparative Example 4 | 91.9 | 89.4 | 92.6 |
| Comparative Example 5 | Not Tested | 95.2 | 98.4 |
| Comparative Example 6 | 100.1 | Not Tested | 98.9 |
| Comparative Example 7 | 101.5 | Not Tested | 101.1 |
| Comparative Example 8 | 98.8 | Not Tested | 101.0 |
| Comparative Example 9 | 100.1 | Not Tested | 99.3 |
| Comparative Example 10 | 101.9 | 100.9 | 101.9 |
| Comparative Example 11 | 100.1 | 98.4 | 98.6 |
| Comparative Example 12 | 100.4 | 98.0 | 98.2 |
| Comparative Example 13 | 101.0 | 97.6 | 97.6 |
| Comparative Example 14 | 91.2 | 101.4 | 98.0 |
| Comparative Example 15 | 98.9 | 101.4 | 100.5 |
| Comparative Example 16 | 100.5 | 97.6 | 101.4 |
| Comparative Example 17 | 99.2 | 98.9 | 106.2 |
| Comparative Example 18 | 99.7 | Not Tested | 100.9 |
| Comparative Example 19 | 101.3 | Not Tested | 96.3 |
| Comparative Example 20 | 98.9 | Not Tested | 100.9 |
| Comparative Example 21 | Not Tested | Not Tested | 99.7 |

The results of the suspensibility tests for each of the Examples and Comparative Examples as described above, both after freeze/thaw cycling and after storage under conditions of elevated temperature, the differences in the suspensibility values between the Examples and the Comparative Examples indicate statistically significant suspensibility is achieved when the polymeric additives of the Examples are used instead of the additives in the Comparative Examples.

Wet Screen Analysis

Wet Screen Analysis is performed according to a procedure described in the CIPAC handbook under Wet Sieving MT 59.3. Initial testing is done as soon as possible after preparing the compositions in the Eiger Mini 50 mill. If the initial testing is satisfactory, a sample is tested that has undergone 6 weeks of freeze/thaw cycling.

To perform the Wet Screen Analysis, 3 inch sieves of 50, 100 and 325 mesh are used and are dried in an oven at 50° Celsius overnight in preparation for the testing. The sieves are weighed individually.

25 gm of the composition is added to a 600 mL beaker, and the beaker is filled to the 400 mL mark with tap water. The contents of the 600 mL beaker are then stirred with a magnetic stirrer for 5 minutes with a minimal vortex.

The stacked sieves are wetted with tap water and the composition is then poured through the sieves. While stacked, the sieves are rinsed with tap water to ensure that all of the composition that can pass through the sieves does so. The sieves are then dried in a 50° Celsius oven overnight, and the sieves are reweighed.

A percent of the composition retained on each sieve is calculated as follows:

Wt. of the Sieve Plus Residue−Wt. of the Sieve=Wt. of the Residue

% Residue=Wt. of Residue/25*100

The percent of the composition retained on each sieve is set forth below in Table 6 (for initial results), Table 7 (for results after storage under conditions of elevated temperature of either 40° or 54° Celsius for a period of 28 days), and Table 8 (for results after freeze/thaw cycling).

TABLE 6

Results of Wet screen test

| Component | Retention on 50 mesh Wet Screen (%) | Retention on 100 mesh Wet Screen (%) | Retention on 300 mesh Wet Screen (%) |
|---|---|---|---|
| Example 1 | 0.00 | 0.04 | 0.00 |
| Example 2 | 0.00 | 0.00 | 0.00 |
| Example 3 | 0.20 | 0.12 | 0.04 |
| Example 4 | 0.04 | 0.00 | 0.04 |
| Example 5 | 0.16 | 0.16 | 0.16 |
| Example 6 | 0.07 | 0.00 | 0.00 |
| Example 7 | 0.14 | 0.14 | 0.00 |
| Example 8 | 0.28 | 0.14 | 0.00 |
| Example 9 | 0.20 | 0.00 | 0.00 |
| Example 10 | 0.12 | 0.04 | 0.08 |
| Comparative Example 1 | 0.04 | 0.04 | 0.08 |
| Comparative Example 2 | 0.00 | 0.00 | 0.00 |
| Comparative Example 3 | 0.00 | 0.00 | 0.04 |
| Comparative Example 4 | 0.20 | 0.04 | 0.08 |
| Comparative Example 5 | 0.04 | 0.04 | 0.04 |
| Comparative Example 6 | 0.16 | 0.04 | 0.04 |
| Comparative Example 7 | 0.04 | 0.16 | 0.00 |
| Comparative Example 8 | 0.00 | 0.08 | 0.08 |
| Comparative Example 9 | 0.04 | 0.04 | 0.04 |
| Comparative Example 10 | 0.00 | 0.00 | 0.00 |
| Comparative Example 11 | 0.08 | 0.08 | 0.00 |
| Comparative Example 12 | 0.00 | 0.00 | 0.00 |
| Comparative Example 13 | 0.04 | 0.00 | 0.00 |
| Comparative Example 14 | 0.16 | 0.12 | 0.08 |
| Comparative Example 15 | 0.06 | 0.00 | 0.11 |
| Comparative Example 16 | 0.00 | 0.16 | 0.16 |
| Comparative Example 17 | 0.08 | 0.00 | 0.04 |
| Comparative Example 18 | 0.04 | 0.04 | 0.04 |
| Comparative Example 19 | 0.12 | 0.00 | 0.00 |
| Comparative Example 20 | 0.04 | 0.08 | 0.04 |

TABLE 7

| Component | Retention on 50 mesh Wet Screen (%) | Retention on 100 mesh Wet Screen (%) | Retention on 300 mesh Wet Screen (%) |
|---|---|---|---|
| Example 1 | 0.00 | 0.00 | 0.04 |
| Example 2 | 0.11 | 0.06 | 0.11 |
| Example 4 | 0.00 | 0.00 | 0.00 |
| Example 5 | 0.22 | 0.00 | 0.04 |
| Example 6 | 0.11 | 0.05 | 0.00 |
| Example 7 | 0.14 | 0.14 | 0.00 |
| Example 8 | 0.28 | 0.14 | 0.00 |
| Comparative Example 1 | 0.00 | 0.00 | 0.00 |
| Comparative Example 3 | 0.00 | 0.00 | 0.00 |
| Comparative Example 4 | 0.08 | 0.04 | 0.08 |
| Comparative Example 10 | 0.04 | 0.00 | 0.00 |
| Comparative Example 11 | 0.04 | 0.00 | 0.00 |
| Comparative Example 12 | 0.00 | 0.05 | 0.05 |
| Comparative Example 13 | 0.04 | 0.00 | 0.04 |
| Comparative Example 14 | 0.12 | 0.00 | 0.08 |
| Comparative Example 15 | 0.13 | 0.00 | 0.04 |
| Comparative Example 16 | 0.00 | 0.05 | 0.00 |
| Comparative Example 17 | 0.20 | 0.12 | 0.00 |

TABLE 8

| Component | Retention on 50 mesh Wet Screen (%) | Retention on 100 mesh Wet Screen (%) | Retention on 300 mesh Wet Screen (%) |
|---|---|---|---|
| Example 1 | 0.04 | 0.04 | 0.04 |
| Example 2 | 0.08 | 0.00 | 0.00 |
| Example 3 | 0.16 | 0.04 | 0.00 |
| Example 4 | 0.04 | 0.00 | 0.00 |

TABLE 8-continued

| Component | Retention on 50 mesh Wet Screen (%) | Retention on 100 mesh Wet Screen (%) | Retention on 300 mesh Wet Screen (%) |
|---|---|---|---|
| Example 5 | 0.00 | 0.00 | 0.00 |
| Example 6 | 0.05 | 0.00 | 0.00 |
| Example 9 | 0.08 | 0.04 | 0.04 |
| Example 10 | 0.20 | 0.32 | 0.08 |
| Example 11 | 0.00 | 0.00 | 0.04 |
| Comparative Example 1 | 0.16 | 0.08 | 0.08 |
| Comparative Example 2 | 0.04 | 0.04 | 0.04 |
| Comparative Example 3 | 0.04 | 0.04 | 0.08 |
| Comparative Example 4 | 1.23 | 0.63 | 0.04 |
| Comparative Example 5 | 0.00 | 0.00 | 0.00 |
| Comparative Example 6 | 0.00 | 0.04 | 0.04 |
| Comparative Example 7 | 0.04 | 0.04 | 0.16 |
| Comparative Example 8 | 0.00 | 0.00 | 0.00 |
| Comparative Example 9 | 0.12 | 0.08 | 0.00 |
| Comparative Example 10 | 0.08 | 0.04 | 0.08 |
| Comparative Example 11 | 0.04 | 0.04 | 0.08 |
| Comparative Example 12 | 0.00 | 0.08 | 0.08 |
| Comparative Example 13 | 0.00 | 0.00 | 0.00 |
| Comparative Example 14 | 0.00 | 0.00 | 0.04 |
| Comparative Example 15 | 0.00 | 0.04 | 0.04 |
| Comparative Example 16 | 0.00 | 0.00 | 0.00 |
| Comparative Example 17 | 0.20 | 0.12 | 0.08 |
| Comparative Example 18 | 0.04 | 0.00 | 0.00 |
| Comparative Example 19 | 0.08 | 0.00 | 0.00 |
| Comparative Example 20 | 0.04 | 0.04 | 0.00 |
| Comparative Example 21 | 0.00 | 0.00 | 0.00 |

The results of the wet screen tests for each of the Examples and the Comparative Examples indicate that the compositions of the Examples performed as well as the compositions of the Comparative Examples, with only negligible amounts of the composition retained.

Preparation of Compositions (Part II)

Table 9 lists the composition of example 22 and the comparative examples 23 (without polymeric additive) to 26. All data in Table 9 are in g/l unless otherwise stated. The compositions of examples 22 to 26 were prepared by mixing all components and milling them on a thermostated bead mill until the desired particle size was reached.

TABLE 9

Results of enhancing pesticidal activity testing

| Component | Ex. 22 | Ex. 23 [2] | Ex. 24 [2] | Ex. 25 [2] | Ex. 26 [2] |
|---|---|---|---|---|---|
| Solvent Constituent A | Ad 1.0 L | Ad 1.0 L | Ad 1.0 L | Ad 1.0 L | Ad 1.0 L |
| Solvent Constituent B | 70 | 70 | 70 | 70 | 70 |
| Wetting Agent C | 30 | 30 | 30 | 30 | 30 |
| Wetting Agent D | 20 | 20 | 20 | 20 | 20 |
| Polymeric Additive A | 100 | — | — | — | — |
| Polymeric Additive E [1] | — | — | 100 | — | — |
| Polymeric Additive F [1] | — | — | — | 100 | — |
| Active substance 4 | 120 | 120 | 120 | 120 | 120 |
| Active substance 5 | 300 | 300 | 300 | 300 | 300 |
| Additional Component A | 5 | 5 | 5 | 5 | 5 |
| Additional Component C | 2 | 2 | 2 | 2 | 2 |
| Additional Component D | 2 | 2 | 2 | 2 | 2 |
| Additional Component E | — | — | — | — | 15 |

[1] polymeric additive for comparison, not according to the invention.
[2] comparative example.
Wetting Agent C is an EO/PO/EO block copolymer (molar mass of PO block about 3200 g/mol, about 50 wt % PE in molecule).
Wetting Agent D is a polymeric sodium salt of alkylnaphthalene sulphonate.
Polymeric Additive E is an C9-C11 alcohol ethoxylate propoxylate (CAS Nr. 103818-93-5), commerically available as Atplus ® 245 from Uniquema.
Polymeric Additive F is a C13 alkyl alcohol alkyxylate ethoxylate.
Active substance 4 is difenoconazole (a fungicide, water solubility 3.3 mg/L at 20° C.).
Active substance 5 is metrafenone (a fungicide, water solubility 0.49 mg/L at 20° C.)).
Additional Component C is an antibacterial agent.
Additional Component D is an xanthan gum.
Additional Component E is an alkoxylated C10-alcohol (the same as used in the preparation of Polymeric Additive A above).

Test of Particle Size After Storage

The stability of the compositions was evaluated by following the average particle size (percentage of particles with size <2 μm, as determined by dynamic light scattering), which was determined initially, and after one week storage at 40° C. or 50° C., respectively (see Table 10). The stability of example 22 according to the invention was as good as the stability without adjuvant (example 23). For comparison, an commercially available adjuvant as in example 24 dramatically reduced the stability of the suspension and the particle size increased heavily.

TABLE 10

Particle Size (percentage of particles with size <2 μm) after storage

| Composition | Initial [%] | After 1 week at 40° C. [%] | After 1 week at 50° C. [%] |
|---|---|---|---|
| Example 22 | 66 | 64 | 53 |
| Comparative Ex. 23 | 66 | 63 | 59 |
| Comparative Ex. 24 | 59 | 24 | 1 |
| Comparative Ex. 25 | 65 | 29 | 4 |

Test of Viscosity After Storage

The stability of the compositions was evaluated by following the viscosity (analyzed) according to specifications of Food and Agricultural Organization (FAO) MT 192, values in mPa·s), which was determined initially, and after one week storage at 40° C. or 50° C., respectively (see Table 11). The stability of example 22 according to the invention was as good as the stability without adjuvant (example 23). For comparison, an commercially available adjuvant as in example 24 and 25 dramatically reduced the stability of the suspension and the viscosity increased heavily.

TABLE 11

Viscosity after storage

|  | Initial [mPa · s] | After 1 week at 40° C. [mPa · s] | After 1 week at 50° C. [mPa · s] |
| --- | --- | --- | --- |
| Example 22 | 351 | 341 | 390 |
| Comparative Ex. 23 | 28 | 27 | 28 |
| Comparative Ex. 24 | 130 | >1000 | >1000 |
| Comparative Ex. 25 | 221 | >1000 | >1000 |

Test of Pesticidal Activity in Greenhouse

The pesticidal activity was tested in a greenhouse on grapes, which were infected with powdery mildew. The plants were treated with the composition of example 22 and example 23 at a dose rate of 1.17, 4.69 or 18.75 ppm. The percentage of the disease was evaluated 21 and 28 days post infection (dpi). The test was made twice and the results are summarized in Table 11 and 12. The data show that the composition of example 22 (with adjuvant) has a higher pesticidal activity compared to the composition of example 23 without adjuvant.

TABLE 11

Pesticidal Activity (Greenhouse)

|  | Dose rate [ppm] | % Disease 21 dpi | % Disease 28 dpi |
| --- | --- | --- | --- |
| Untreated control | — | 17 | 39 |
| Example 22 | 18.75 | 0.2 | 0 |
| Example 22 | 4.69 | 2.5 | 0.6 |
| Example 22 | 1.17 | 4.4 | 4 |
| Comparative Ex. 23 | 18.75 | 0.1 | 0 |
| Comparative Ex. 23 | 4.69 | 2.1 | 0.6 |
| Comparative Ex. 23 | 1.17 | 11 | 14 |

TABLE 12

Pesticidal Activity (Greenhouse)

|  | Dose rate [ppm] | % Disease 21 dpi | % Disease 28 dpi |
| --- | --- | --- | --- |
| Untreated control | — | 43 | 57 |
| Example 22 | 18.75 | 0 | 0 |
| Example 22 | 4.69 | 0.3 | 0.3 |
| Example 22 | 1.17 | 0.8 | 4.6 |
| Comparative Ex. 23 | 18.75 | 0 | 0.3 |
| Comparative Ex. 23 | 4.69 | 0.1 | 0 |
| Comparative Ex. 23 | 1.17 | 4 | 8.3 |

Test of Pesticidal Activity in a Field

The pesticidal activity was tested in a field with cucumbers, which were infected with powdery mildew. The plants were treated with the composition of example 22 and example 23 at a dose rate of 1.17, 4.69 or 18.75 ppm. The percentage of the disease on the upper and lower side of the leaves was evaluated 6 days after application (DAA). The tests were made twice and the results are summarized in Table 13 (6 DAA) and 14 (8 DAA), which show that the composition of example 22 (with adjuvant) has a higher pesticidal activity compared to the composition of example 23 without adjuvant.

TABLE 13

Pesticidal Activity (Field)

|  | Dose rate [g/ha] | % Disease Leaves upperside | % Disease Leaves underside |
| --- | --- | --- | --- |
| Untreated control | — | 53 | 63 |
| Example 22 | 140 | 0.5 | 27 |
| Example 22 | 105 | 0.3 | 14 |
| Comparative Ex. 23 | 140 | 0.4 | 31 |
| Comparative Ex. 23 | 105 | 0.4 | 26 |

TABLE 14

Pesticidal Activity (Field)

|  | Dose rate [g/ha] | % Disease Leaves underside |
| --- | --- | --- |
| Untreated control | — | 68 |
| Example 22 | 140 | 5 |
| Example 22 | 105 | 8 |
| Comparative Ex. 23 | 140 | 15 |
| Comparative Ex. 23 | 105 | 23 |
| Comparative Ex. 24 | 140 | 7 |
| Comparative Ex. 24 | 105 | 11 |
| Comparative Ex. 25 | 140 | 6 |
| Comparative Ex. 25 | 105 | 8 |
| Comparative Ex. 26 | 140 | 14 |
| Comparative Ex. 26 | 105 | 24 |

Obviously, many modifications and variations of the instant invention are possible in light of the above teachings. It is, therefore, to be understood that within the scope of the appended claims, the invention may be practiced otherwise than as specifically described.

Testing the Enhancing Retention of Active Substances on Plants

An aqueous suspension concentrate containing 300 g/l fluxapyroxad, dispersing agent, anti-foamant, xanthan gum thickener, bactericide, and 1,2-propylene glycol antifreezing was prepared (called "SC Blank"). Optionally, Polymeric Additive A was added. To measure the retention of an aqueous spray, the suspension concentrated was diluted with water and a fluorescence tracer (fluoresceine) to prepare a sprayable tank mix. Said tank mix was applied with a rate of 200 l/ha vie nozzle set (nozzle type: flat fan (air induction), ID 120 02, Lechler) at a speed of 1.4 m/s with a pressure of 3.4 bar and a spray boom (1 m, 3 nozzles; nozzle distance 50 cm). The tank mix was applied to wheat (var. Melon) at the growth stage BBCH 12. After application the leaves of the plants were collected and washed with a defined amount of washing solution (0.1 mol/l NaOH). The fluorescence intensity, which is proportional to the amount of active retained on leaves, was measured with a fluorometer. Each experiment was repeated four times and the average values are given in Table 15. The data show that the retention on the plants is increased due to the Polymeric Additive A compared to formulations without this additive or compared to water.

TABLE 15

Retention on plant

| Applied composition | Spray retention on plant [Fluorescence intensity per g plant material and per ml washing solution] |
|---|---|
| Water [1] | 1070 |
| SC Blank [1] | 1228 |
| SC Blank + 0.1% Polymeric Additive A [2] | 1830 |
| SC Blank + 0.2% Polymeric Additive A [2] | 2459 |

[1] comparative, not according to the invention.
[2] concentration in tank mix.

What is claimed is:

1. A composition comprising:
a pesticide; and
a non-crosslinked polymeric additive comprising:
  1) at least one unit represented by the formula (I):

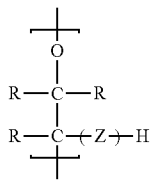

(I)

wherein each R is independently selected from the group of a hydrogen atom, a C1 to C5 alkyl group, and combinations thereof; and Z comprises a group according to formula (II):

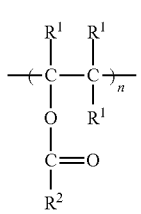

(II)

wherein n is an integer ≥10;
wherein each $R^1$ is independently selected from the group of a hydrogen atom, an alkyl group, and combinations thereof; and $R^2$ is a $C_1$-$C_{10}$ hydrocarbon group; and
  2) at least one unit represented by the formula (III):

(III)

wherein A is an alkyleneoxy group having from 2 to 10 carbon atoms;
wherein the composition is an aqueous suspension and pesticide is present in form of solid particles which are suspended in said aqueous suspension.

2. The composition as set forth in claim 1 wherein said group represented by the formula (II) is present in said polymeric additive in an amount of from 45% to 75% by weight based on the total weight of said polymeric additive.

3. The composition as set forth in claim 1, wherein said polymeric additive has a number average molecular weight of from 5,000 to 200,000 g/mol.

4. The composition as set forth in claim 1 wherein each R is independently selected from the group of a hydrogen atom, a methyl group, or combinations thereof, and A is an alkyleneoxy group having from 2 to 3 carbon atoms.

5. The composition as set forth in claim 1 wherein $R^1$ is a hydrogen atom.

6. The composition as set forth in claim 1 wherein $R^2$ is a methyl group.

7. The composition as set forth in claim 1 wherein said polymeric additive is present in an amount of at least 0.5 percent by weight based on the total weight of said composition.

8. The composition as set forth in claim 1 wherein said polymeric additive is present in an amount of at least 5 percent by weight based on the total weight of said composition.

9. A method of preparing a composition as defined in claim 1 comprising the step of combining the pesticide and the polymeric additive to form the composition.

10. The method as set forth in claim 9 further comprising the step of combining a grinding media with at least one of the pesticide and/or the polymeric additive when the pesticide is in solid particle form.

11. A method for controlling phytopathogenic fungi and/or undesired plant growth and/or undesired attack by insects or mites and/or for regulating the growth of plants, where the composition as defined in claim 1 is allowed to act on the particular pests, their habitat or the plants to be protected from the particular pest, the soil and/or on undesired plants and/or the useful plants and/or their habitat.

12. The method of claim 11, wherein said polymeric additive has a number average molecular weight of from 5,000 to 200,000 g/mol.

13. The method of claim 11, wherein each R is independently selected from the group of a hydrogen atom, a methyl group, or combinations thereof, and A is an alkyleneoxy group having from 2 to 3 carbon atoms.

14. The method of claim 11, wherein $R^1$ is a hydrogen atom.

15. The method of claim 11, wherein $R^2$ is a methyl group.

16. A method of enhancing the pesticidal activity of a pesticide comprising combining the pesticide with a non-crosslinked polymeric additive;
wherein said polymeric additive comprises:
  1) at least one unit represented by the formula (I):

(I)

wherein each R is independently selected from the group of a hydrogen atom, a C1 to C5 alkyl group, and combinations thereof; and Z comprises a group according to formula (II):

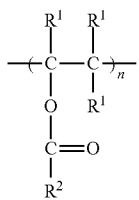

(II)

wherein n is an integer $\geq 10$ wherein each $R^1$ is independently selected from the group of a hydrogen atom, an alkyl group, and combinations thereof; and $R^2$ is a $C_1$-$C_{10}$ hydrocarbon group; and 2) at least one unit represented by the formula (III):

(III)

wherein A is an alkyleneoxy group having from 2 to 10 carbon atoms;

wherein the pesticide is present in form of solid particles which are suspended in an aqueous suspension.

17. The method as set forth in claim 12, wherein the amount of the polymeric additive is in the range of from 10 to 500 wt %, based on the weight of the pesticide.

18. The method of claim 17, wherein the polymeric additive comprises:

1) at least one unit represented by the formula (I):

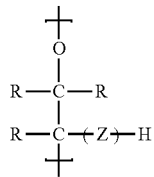
(I)

wherein each R is independently selected from the group of a hydrogen atom, a C1 to C5 alkyl group, and combinations thereof; and Z comprises a group according to formula (II):

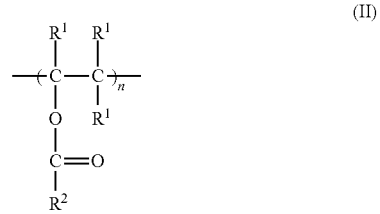
(II)

wherein n is an integer $\geq 10$ wherein each $R^1$ is independently selected from the group of a hydrogen atom, an alkyl group, and combinations thereof; and $R^2$ is a $C_1$-$C_{10}$ hydrocarbon group; and 2) at least one unit represented by the formula (III):

(III)

wherein A is an alkyleneoxy group having from 2 to 10 carbon atoms.

19. The method of claim 18, wherein said polymeric additive has a number average molecular weight of from 5,000 to 200,000 g/mol.

20. The composition as set forth in claim 1, wherein the water content of the composition is from 10 to 80 wt %;

the pesticide has a solubility in water of less than 10 g/L at 20° C.;

the total amount of all pesticides present in the composition is from 10 to 60 wt %;

the amount of the polymeric additive is in the range of from 5 to 1000% based on the weight of the pesticide.

* * * * *